(12) United States Patent
Ma et al.

(10) Patent No.: US 6,679,843 B2
(45) Date of Patent: Jan. 20, 2004

(54) ADAPTIVE ULTRASOUND IMAGE FUSION

(75) Inventors: Qinglin Ma, Bellevue, WA (US);
Rodney L. Boleyn, Renton, WA (US);
King Yuen Wong, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/179,080

(22) Filed: Jun. 25, 2002

(65) Prior Publication Data

US 2003/0236460 A1 Dec. 25, 2003

(51) Int. Cl.$^7$ ................................................. A61B 8/06
(52) U.S. Cl. ....................................................... 600/441
(58) Field of Search ............................... 600/440–441, 600/443, 447, 453–456; 128/916

(56) References Cited

U.S. PATENT DOCUMENTS

| | | |
|---|---|---|
| 5,285,788 A | 2/1994 | Arenson et al. |
| 5,921,931 A * | 7/1999 | O'Donnell et al. ......... 600/441 |
| 5,931,784 A * | 8/1999 | Kajiwara et al. ........... 600/441 |
| 5,961,460 A * | 10/1999 | Guracar et al. ............. 600/440 |
| 6,419,632 B1 * | 7/2002 | Shiki et al. ................. 600/443 |

* cited by examiner

Primary Examiner—Francis J. Jaworski

(57) ABSTRACT

Elevation fold-in artifact is reduced by combining Doppler and B-mode image signals. The B-mode image signals and Doppler image signals are combined using a modulated, non-linear function. Portions of the B-mode image signal associated with stationary tissue are intact while portions of the B-mode image signal associated with flow are substantially suppressed. The suppression is gradual rather than binary to avoid flash artifacts, such as providing an adaptive modulated, non-linear combination function. Doppler or flow image signals are less sensitive than tissue or B-mode signals to elevation beam width. Suppressing the B-mode image signal where flow exists better identifies small vessels that would otherwise be characterized as tissue. Small vessel or other small structure information associated with moving fluid is inserted within the gray-scale or B-mode image. Clutter within large vessels is more likely mapped to black or removed. The pathology is kept intact by not removing stationary tissue information. The enhanced large vessel presentation and added visibility of small vessels provides more detail about tissue morphology for radiology applications. The resulting gray-scale image appears as if fine or narrow beams had been used in both the azimuth as well as the elevation directions. Unlike a true narrowing of the elevation beam at a focal point, the enhanced imaging is provided over an entire field of view, and is not probe dependent. The enhanced imaging could be a software solution.

34 Claims, 3 Drawing Sheets

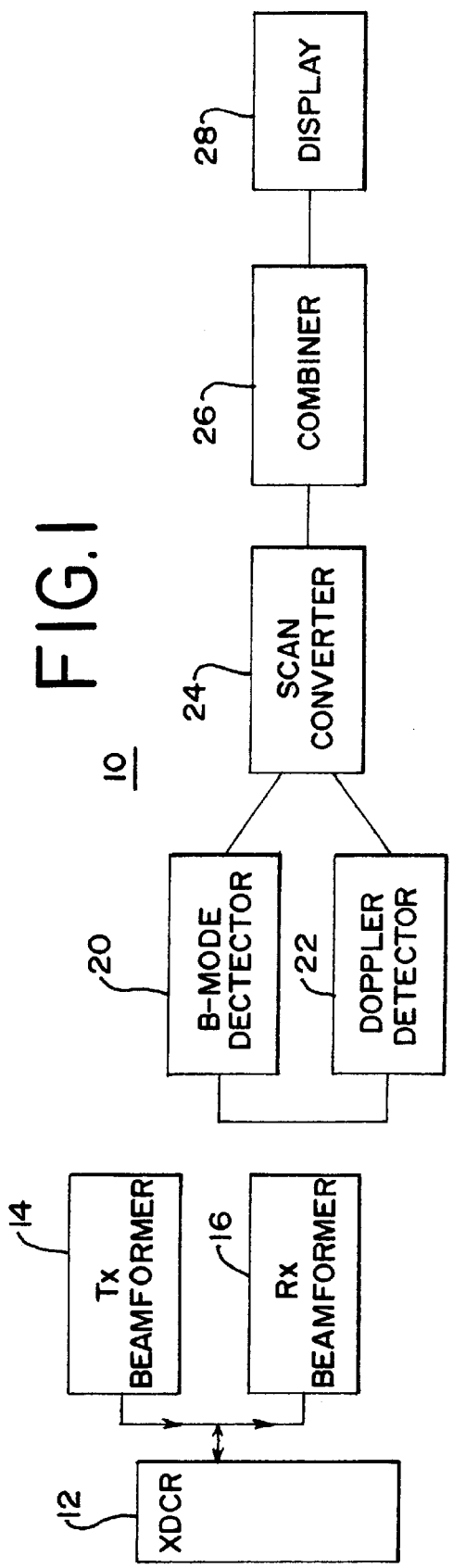
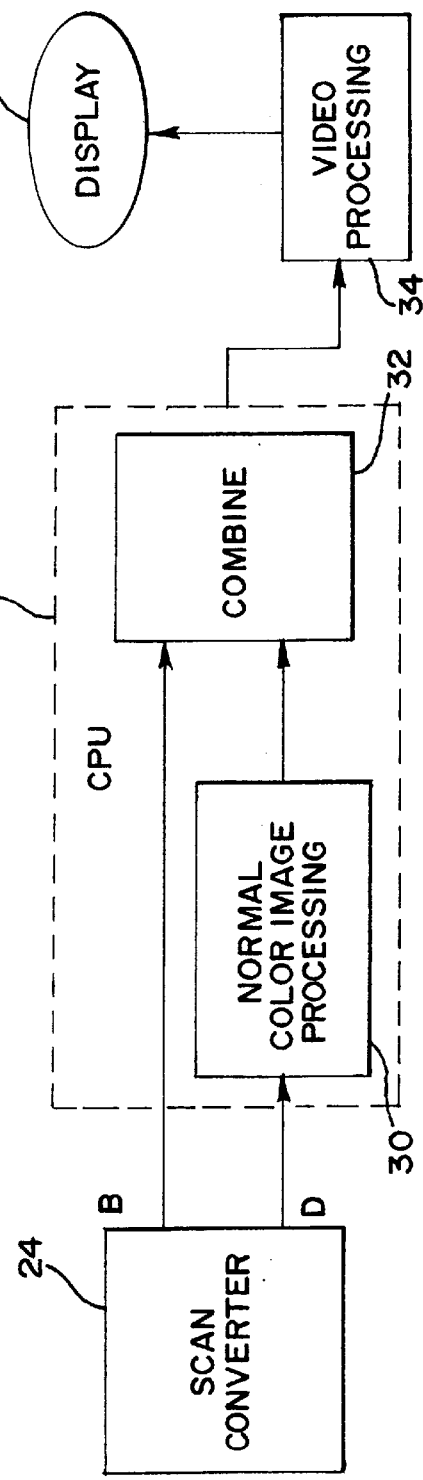

ADAPTIVE ULTRASOUND IMAGE FUSION

BACKGROUND

The present invention relates to ultrasound imaging. In particular, ultrasound imaging using different sources of information for reducing clutter or artifacts and adding missing small blood vessels back to the grayscale image is provided.

Ultrasound images are typically generated in response to acoustic beams electronically steered in an azimuth dimension and mechanically focused in an elevation dimension. In general, the elevation beam width is an order of one magnitude wider than azimuthal beam width. The elevation beam width varies as a function of range and includes signals from within the entire beam width. Wider beam widths increase unwanted signal or noise. The elevation beam width artifact decreases the contrast and obscures real structures, such as small vessels, cysts and the heart apex. The elevation beam width may result in clutter or weak signals indicating tissue within a large vessel or pool of fluid, such as near vessel walls. This elevation fold-in artifact confuses pathology with clutter and results in small vessels being not visible.

Narrower elevation beam width is provided using 1.5 dimensional or 2-dimensional transducer arrays. A narrower elevation beam width provides, more likely identification of small structures and cleaner large vessel. However, 1.5 dimensional and 2-dimensional transducer arrays require complicated manufacturing processes, additional system hardware and it is a probe specific solution. These complications increase the overall cost of an ultrasound system.

To further distinguish fluid, such as blood, from tissue in radiology imaging, a Doppler image representing velocity or power is overlaid on the B-mode or gray-scale image. Doppler information is thresholded to determine the presence of flow or tissue at each pixel or image location. Where sufficient flow is identified, the Doppler information is displayed in color instead of the B-mode information.

Doppler imaging or color flow imaging introduces different artifacts, such as a color flash artifact. Breathing, heart beating, muscle movement or other movement causes false detection of flow. Even without flash artifact, a jagged vessel boundary or strong discontinuity is created by the binary flow decision. The color Doppler information is intrusive, resulting in removing, overriding or otherwise altering B-mode border or vessel boundary information. Generally, Doppler images have worse resolution than grayscale images.

As an alternative to the binary criteria for distinguishing between flow and tissue, flow and tissue information maybe blended. A transparent color map superimposes the flow information on a B-mode or tissue information. For example, a white value or other characteristic of the Doppler color is altered as a function of a B-mode signal associated with the interior of a vessel or other fluid region. Various functions maybe used for the blending, such as a function that emphasizes tissue for low values of Doppler signal and quickly transverses to emphasizing Doppler signals for a midrange of B-mode values and provides strong emphasis on color information for low B-mode values. However, tissue and fluid borders are not as clearly defined or as sharp as more conventional B imaging. Another combination provides for mapping Doppler power information to grayscale values with the tissue information. Some clutter may be removed but the vessel or pathology boundary is jagged or otherwise undesirable. This blending of Color and grayscale pixel further obscures the border.

A combination of both Doppler and B-mode image signals may remove some artifacts in cardiac imaging. U.S. Pat. No. 5,961,460 to Guracar, et al. discloses combinations of B-mode and Doppler image signals for enhancing moving tissue, such as heart valves or heart walls, and suppressing or removing information associated with clutter and stationary tissue. A modulated, non-linear function of both the B-mode and Doppler image signals is provided by a look-up table structure.

BRIEF SUMMARY

The present invention is defined by the following claims, and nothing in this section should be taken as a limitation on those claims. By way of introduction, the preferred embodiments described below include methods and systems for ultrasonic B-mode imaging with different signals for artifact reduction and organ morphology enhancement. The B-mode image signals and Doppler image signals are combined using a modulated, non-linear function. The end results are displayed in grayscale or superimposed with other kind of image. Portions of the B-mode image signal associated with stationary tissue are intact while portions of the B-mode image signal associated with flow are substantially suppressed. The suppression is pixel-by-pixel and gradual rather than binary to avoid flash artifacts, such as providing an adaptive modulated, non-linear combination function. Doppler or flow image signals are less sensitive than tissue or B-mode signals to elevation beam width. Suppressing the B-mode image signal where flow exists better identifies small vessels that would otherwise be characterized as tissue. Small vessel or other small structure information associated with fluid is inserted within the gray-scale or B-mode image. Clutter within large vessels is more likely mapped to black or removed. The pathology is kept intact by not removing stationary tissue information. The enhanced large vessel presentation and added visibility of small vessels provides more detail about tissue morphology for radiology applications. The resulting gray-scale image appears as if fine or narrow beams had been used in both the azimuth as well as the elevation directions. Unlike a true narrowing of the elevation beam at a focal point, the enhanced imaging is provided over an entire field of view.

In a first aspect, individual display indicia are provided as a modulated, non-linear function of both Doppler and B-mode image signals representing a same region. The non-linear function substantially enhances portions of the B-mode image signal associated with stationary tissue and substantially suppresses portions of the B-mode image signal associated with flow.

In a second aspect, one of a processor or dedicated mixing circuit is provided for implementing a modulated, non-linear function. The outputs from B-mode and Doppler detectors are provided for combination by the processor or mixing circuitry.

In a third aspect, individual display indicia are generated representing a modulated, non-linear function of both Doppler and B-mode signals. The nonlinear function modulates one of the B-mode and Doppler image signals with a weighted other one of the Doppler and B-mode signals. For example, a B-mode signal is modulated with a Doppler signal. Conversely, a Doppler signal is modulated by the B-mode signal.

In a fourth aspect, individual display indicia are generated representing an imaged region as a function of both Doppler and B-mode signals. One of the Doppler and B-mode image signals is modulated by the same Doppler or B-mode image signal. For example, a Doppler signal is modulated by a weight or other variable adaptively responsive to the Doppler signal. In another example, a B-mode image signal is modulated by a weight adaptively responsive to the B-mode image signal.

Further aspects and advantages of the invention are discussed below in conjunction with the preferred embodiments.

BRIEF DESCRIPTION OF SEVERAL VIEWS OF THE DRAWINGS

The components in the Figures are not necessarily to scale, emphasis instead being placed upon illustrating the principles of the invention. Moreover, in the Figures, like reference numerals designate corresponding parts throughout the different views.

FIG. 1 is a block diagram of one embodiment of a system for ultrasonic imaging using different signals.

FIG. 2 is a block diagram of one embodiment of a processor for combining Doppler and B-mode image signals.

DETAILED DESCRIPTION OF THE PREFERRED EMBODIMENTS

Figure 3:
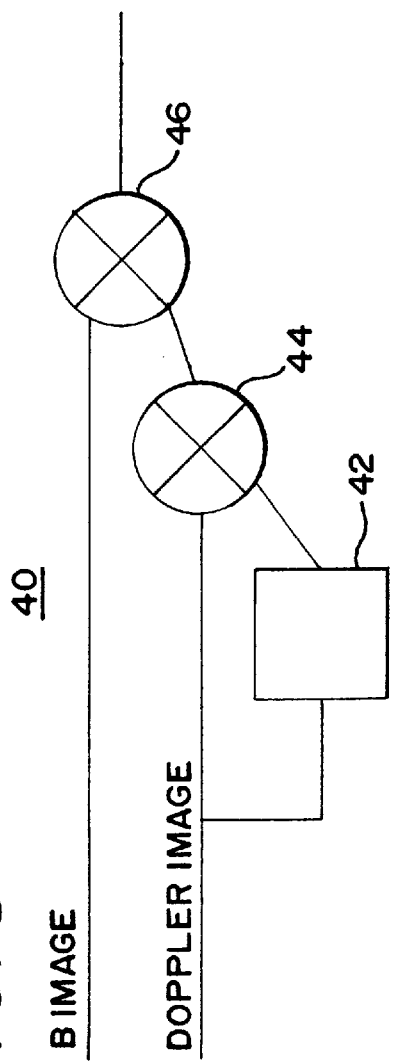
FIG. 3 is a block diagram of one embodiment of a mixing circuit for combining B-mode and Doppler image signals.

B-mode and Doppler image signals are combined using a modulated, non-linear function. Stationary tissue and other tissue are enhanced relative to clutter by suppressing B-mode image signals where flow exists. The modulated, non-linear function allows for optimized clutter removal in large vessels and identification of small vessels within a gray-scale or B-mode image for radiology applications. Since Doppler image signals are less sensitive than B-mode image signals to elevation beam width artifacts, the Doppler image signals more likely identify small vessel structures. This better sensitivity is used for B-mode imaging to add (i.e. to reduce the intensity) gray-scale signals representing smaller vessel structures. In alternative embodiments, the modulated, non-linear combination is implemented in cardiology applications, such as for imaging moving heart structures. In yet other alternative embodiments, the modulated, non-linear function generates color display indicia.

A wide variety of ultrasonic imaging systems may be adapted for implementing one or more of the combinations of B-mode and Doppler image signals discussed herein. FIG. 1 shows one embodiment for a suitable ultrasound imaging system 10. The imaging system 10 includes an ultrasonic transducer 12. The transducer 12 comprises a single element, one dimensional array of elements, 1.5 or 2-dimensional array of elements or other array of now known or later developed piezoelectric or micro-electro-mechanical devices. The transducer 12 converts electrical ultrasonic frequency signals into sound energy, which is then emitted into a tissue, such as an organ, muscle, or vessel. Acoustic energy reflected from the tissue is converted back to electrical signals by the transducer 12.

A transmit beam former 14 generates transmit wave forms that are applied to the transducer 12. In response, the transducer 12 forms transmit beams of ultrasonic energy, centered at a selected fundamental frequency.

Receive signals generated by the transducer 12 in response to reflected energy are formed into receive beams by a receive beam former 16. The region from which reflected energy is formed into receive beams will be referred to as an imaged region, and may include blood, tissue, and optionally a non-linear contrast agent. The receive beam former 16 may be responsive to energy at a same frequency as that applied to the transducer 12 by the transmit beam former 14 (the fundamental frequency) or at a different frequency which may be harmonically related to the transmit frequency (a harmonic frequency). The beam-formed signals are in an in-phase and quadrature (I/Q) format, but may be output as radio frequency or other signals for application to one or both of a B-mode detector 20 and a Doppler detector 22.

The B-mode detector 20 comprises one or more of a processor, a digital signal processor, an application specific integrated circuit, an analog device, a digital logic device, or combinations thereof for detecting an intensity or envelope characteristic of a received signal. In one embodiment, the B-mode detector 20 comprises a mixer, log compressor and control circuits for outputting a B-mode image signal representing tissue. The B-mode detector 20 converts the received signals into detected and log compressed image signals.

The Doppler detector 22 comprises one or more of a processor, a digital signal processor, an application specific integrated circuit, an analog device, a digital logic device and combinations thereof. In one embodiment, the Doppler detector 22 comprises a clutter filter, a corner turning memory, and an estimator for generating estimates of velocity, energy, variance or other motion related estimates. While "Doppler" is used herein, auto-correlation, cross-correlation or other time or frequency based techniques for identifying motion are included within the term Doppler. The Doppler detector estimates Doppler signal velocity and energy parameters. The corner turning memory stores beam-formed samples until a sufficient number of signals have been accumulated to allow Doppler measurements to be made. The clutter filter comprises a high pass or band pass filter to optionally provide greater rejection of signals from stationary and slowly moving objects, such as associated with tissue movement. For Doppler tissue imaging, the clutter filter is bypassed or otherwise programmed to pass information associated with moving tissue. The Doppler parameter estimator estimates the mean velocity and the total energy of the Doppler signal. The velocity and energy signals are thresholded to reject signals from stationary or slowly moving objects. Either of a velocity threshold, energy threshold or combinations of both may be used. The thresholds are determined as a function of the application. If either of the velocity or energy parameters is below a respective threshold, then both parameters representing that same location may be rejected or set to zero. User control of gain for a log detected energy signal as well as a depth gain variable may be implemented after estimation. The energy signal is log compressed to reduce the dynamic range of the signal. Both velocity and energy signals may be spatially filtered to remove noise and dropouts due to speckle and other variations. In alternative embodiments, only velocity estimates or only energy estimates are output.

The B-mode detector 20 and Doppler detector 22 generate B-mode and Doppler image signals, respectively, representative of the imaged region. The image signals are provided to one or more scan converters 24. Separate digital scan converters may be provided for the B-mode and Doppler signals, or a same scan converter 24 is used. The scan converter 24 converts the signals from an acoustic grid to a raster grid suitable for display. The scan converted image signals are output to a combiner 26.

The combiner 26 comprises one or more digital signal processors, application specific integrated circuits, analog devices, digital logic devices and combinations thereof. In alternative embodiments, the combiner 26 is positioned prior to the scan converter 24. In yet other alternative embodiments, the combiner 26 is implemented as part of another component, such as the scan converter 24.

In one embodiment, the combiner 26 comprises a look-up table and associated video memory and multiplexer. For example, the look-up table structures and other systems disclosed in U.S. Pat. No. 5,961,460, the disclosure of which is incorporated herein by reference, are used. In alternative embodiments, a color mapping memory and associated control structure are provided. For example, the scan converter 24 outputs a multiple bit pixel code that is a combination of the B-mode and Doppler image signals. The pixel code is then mapped into a gray-scale or non-gray-scale color using a color map that incorporates the combining function. Look-up table or color map structures allow the implementation of any of various possible combination functions.

In another embodiment, the combiner 26 comprises a general or digital signal processor. FIG. 2 shows one embodiment of the combiner 26 implemented with a processor. For example, a combiner 26 comprises a central processing unit, control processor or other programmable processor within the system 10. The B-mode and Doppler image signals are transferred to the processor 26. The processor 26 implements various color image processing, such as thresholding, filtering, selecting or other Doppler processes in functional block 30. In alternative embodiments, the Doppler processing is implemented in the Doppler detector 22. In functional block 32, the Doppler and B-mode image signals are combined according to a programmable function, such as a modulated, non-linear combination function discussed below. The processor 26 then outputs the combined information for video processing by a video processor 34 and eventually display of an image on a display device 28. In alternative embodiments, the processor 26 implements any video processing and outputs directly to the display 28. Using the processor 26 for implementing the combination 32 allows for flexible programming or implementation of the combination function and other data manipulation.

In yet another alternative embodiment, the combiner 26 comprises a mixing circuit. For example, FIG. 3 shows a mixing circuit 40 of dedicated analog or digital circuits. In one embodiment, the mixing circuit 40 comprises an application specific integrated circuits integrated with scan converter circuitry as part of a signal processing path. A plurality of separate devices implements the combination function. For example, a plurality of multiplexers is provided for selectively routing B-mode and Doppler image signals and weights to various multipliers 42, 44, and 46. Adders, delays or memory buffers, or other devices may also be included for implementing an affine transform or a modulated, non-linear combination function. For example, one multiplier 42 is provided for weighting a normalized Doppler image signal. The weighted Doppler image signal is then multiplied with the Doppler image signal by the multiplier 44 to modulate the Doppler image signal as a function of the Doppler image signal. Alternatively, the B-mode image signal is modulated as a function of the B-mode image signal. Another multiplier 46 multiplies the output of the multiplier 44 with the B-mode image signal. In alternative embodiments, the other multiplier 46 multiplies the output of the multiplier 44 with a Doppler image signal. In alternative embodiments, the multiplier 46 is replaced with an adder to sum the output of the multiplier 44 with the B-mode image signal. The mixing circuit 40 outputs a value representing a gray-scale intensity. The dedicated circuitry of the mixing circuit 40 may allow for some programming, but likely provides less programmability than implementing the combiner 26 with a processor.

The combiner 26 is operable to calculate or generate individual display indicia representative of the imaged region as a modulated, non-linear or other function of both the Doppler and B-mode image signals. In one embodiment, the modulated, non-linear function substantially enhances or maintains portions of the B-mode image signal associated with stationary tissue and substantially suppresses portions of the B-mode image signal associated with flow. As used herein, "enhance" or "maintain" includes passing unaltered or providing minimal reduction relative to suppressed signals. For example, a B-mode image signal is enhanced or maintained when multiplied with a 0.75 or greater weighting. Suppression is used herein to represent relative reduction, such as multiplying a B-mode image signal with a 0.75 or lower weighting. "Substantially" accounts for the range of possibilities for enhancement and suppression and electrical or mechanical implementation variations.

For combination, one of the Doppler and B-mode image signals is modulated as a function of the same or other of the B-mode or Doppler image signal as discussed below. For example, the Doppler image signal is weighted or multiplied by a weight. The weight may be adaptive, such as selecting the weight as a function of the same of the Doppler or B-mode image signals. Additionally or alternatively, one of the Doppler or B-mode image signals is modulated as a function of the other of the Doppler or B-mode image signals. For example, B-mode image signal is multiplied by the weighted Doppler image signal. The modulation is implemented as a multiplication function. In alternative embodiments, linear or other functions are implemented for combining the Doppler and B-mode image signals.

The image signal output by the combiner 26 is provided to the display 28. The image signal comprises a gray-scale, tissue or B-mode image. In alternative embodiments, the image signal output by the combiner 26 comprises a color, RGB, or YUV signal. The combined signal may be further overlaid with a Doppler or other signal or may overlay a B-mode or other signal. For example, the combiner 26 outputs image signals representing tissue structure as a B-mode image. A Doppler color image is then superimposed on the combined image signal. The resulting images are displayed.

Figure 4:
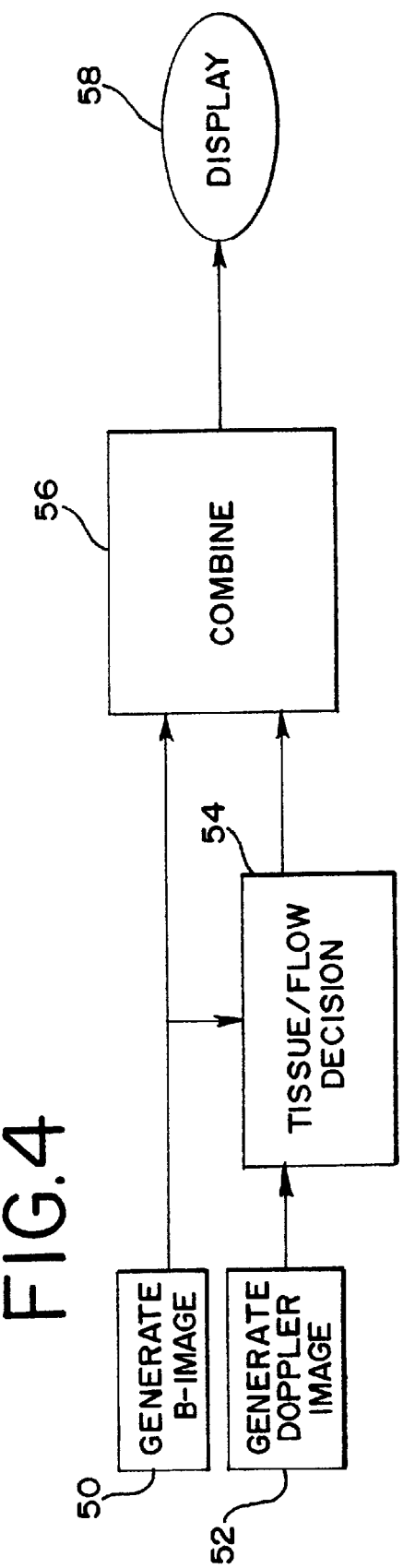
FIG. 4 is a flow diagram of one embodiment for the combination of B-mode and Doppler image signals.

FIG. 4 shows a flow chart of one embodiment for implementing the combination of B-mode and Doppler image signals discussed herein. In act 50, B-mode image signals representing the imaged region are generated. B-mode image signals comprise a frame of harmonic information, fundamental information, spatially filtered information, temporally filtered information, unprocessed intensity information, or other signals representing tissue.

In act 52, the Doppler image signals representing the same imaged region is generated. The Doppler image signals comprise a frame of velocity, energy, variance or other flow estimates for various spatial locations. The estimates are processed using any filtering, thresholding or other processes, or are unprocessed as output by a Doppler estimator.

The system 10 is configured for imaging with both B-mode and Doppler images. For example, the system 10 is configured for imaging pursuant to a color Doppler overlay of a B-mode grayscale image. In one embodiment, dual images are shown. One image shows Doppler image signals superimposed over a B-mode image signal. Adjacently, an image rendered from combinations discussed herein is provided. Accordingly, the user instinctively makes adjustments to the superimposed Doppler and B-mode image to effect changes in the fuse or modulated, non-linear combination image. For example, users are typically trained to or through experience can identify when a power or Doppler gain is set too high such that the B-mode image is distorted. The user then reduces the color or power gain or shifts the pulse repetition frequency upward to reduce flash. The resulting Doppler image signal is then also used for generating the fused image or combined image discussed herein.

In act 54, the Doppler image signal is thresholded to identify Doppler image signals associated with tissue and flow. For example, application specific velocity and/or energy thresholds are applied as discussed above. A resulting frame of data of a single type of estimate, such as velocity or energy is output. In alternative embodiments, multiple types of Doppler estimates are output.

In act 56, the B-mode and Doppler image signals are combined to generate individual display indicia representative of the imaged region. For example, a B-mode image signal and a Doppler image signal representing a same spatial location are combined using a modulated, non-linear function of both the Doppler and B-mode image signals. Various combination functions may be implemented. In one embodiment, a B-mode or gray-scale signal is output according to the function:

$$B_{out} = B_{in}(1 - \alpha^* f(D)), \quad (1)$$

where $B_{out}$ is the combined output signal or display indicia, $B_{in}$ is the B-mode image signal or B-mode brightness, D is the original Doppler image, f is a remapping function which is normalized to be within the range of 0 to 1, and $\alpha$ is a weight which controls how much the Doppler information impacts the tissue brightness when the flow power or velocity changes. This combination adjusts for or avoids color flash artifact and removes some elevation beam width fold-in artifact from the B-mode image signal. In equation (1) above, the B-mode image signal is modulated by the Doppler image signal. In alternative embodiments, the Doppler image signal is modulated by the B-mode image signal.

Figure 5:
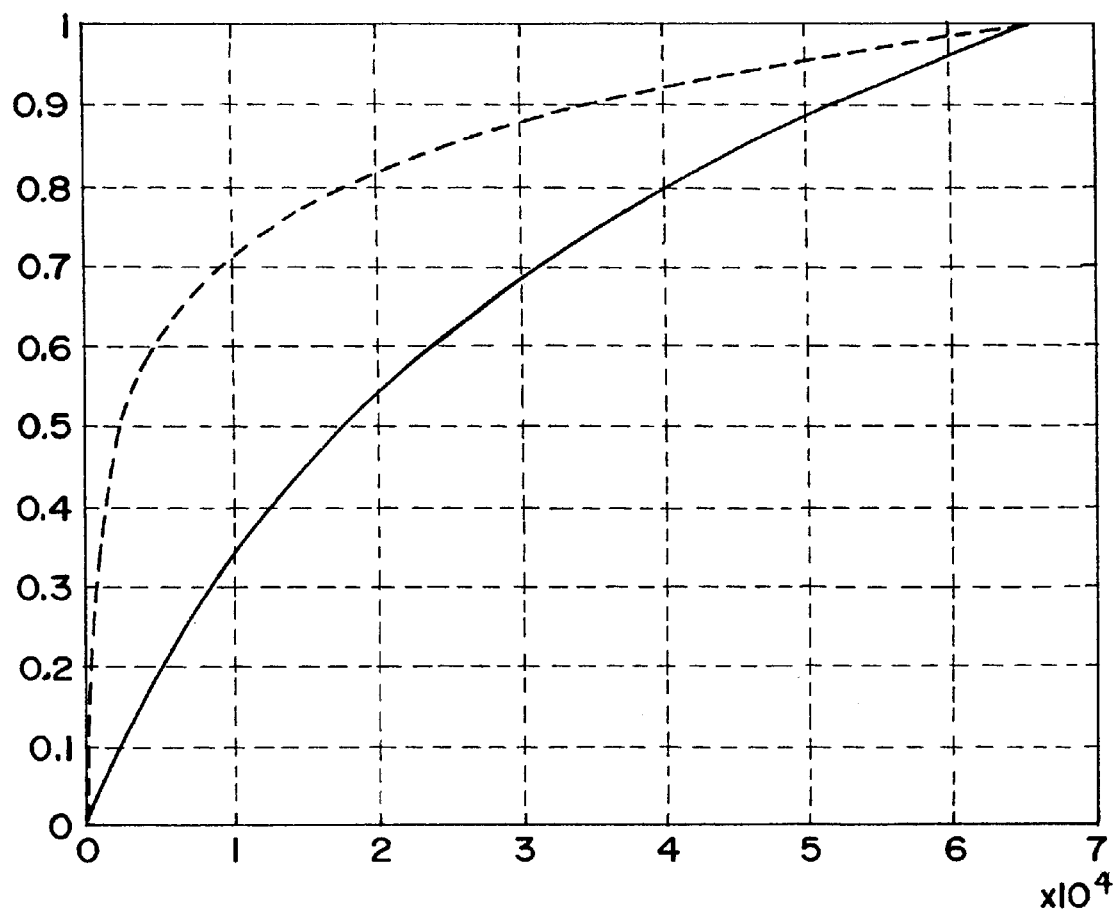
FIG. 5 is a graphical representation of two embodiments of mapping functions with different degree of compression.

The purpose of the function f is to adjust the Doppler signal to emphasize and/or deemphasize strong and/or weak flow in order to provide a natural look with the B-mode signal. For example, in a kidney image where both the arcuates and artery are present, the Doppler signal is very strong in the artery but very weak in the arcuates. Without any remapping function, in order to provide any meaningful blending of the arcuates, the artery may be over blended. On the other hand, if the artery is to be blended more naturally, the blending of the arcuates may be too weak to have any visible effects. By applying a non-linear transfer mapping, for example, a logarithmic compression, the weak arcuates may be emphasized while the artery flow may be deemphasized, creating a better balance between the two. FIG. 5 shows examples of mapping functions with different degree of compression. Finally, the Doppler image signal is normalized by dividing the Doppler image signal by the maximum Doppler value, such as a 255 value. Other normalization functions may be used. While normalization to unity is shown, other normalization functions resulting in different ranges, such as ranges with a maximum value above or below 1, may be used. In alternative embodiments, the B-mode image signal is normalized.

The weight, $\alpha$, modulates the Doppler image signal. The weight adapts as a function of a value. Any of various values may be used, such as the B-mode or Doppler image signals. For example, the weight adapts as a function of Doppler image signal for modulating or multiplication with the Doppler image signal. For example, as the Doppler image signal increases, the weight decreases. In alternative embodiments, more complex functional relationships between the Doppler image signal and the weight are provided. For example, application specific functions are used. In general, where the Doppler value is very low, the weight value is also low to avoid flash artifacts being modulated into the B-mode information. In one embodiment, the weight value increases linearly with increases in the power value to a certain point and then a same weight value is used for midrange power values. For higher power values, a different, such as lower weight value is used. Different functional endpoints and starting points may be provided, as well as different functional relationships. The weight is a value between 0 and 1, but other ranges may be provided. The weight effectively controls the sensitivity. In one embodiment, for strong flow signals such as associated with a large vessel, the weight is selected as a high value so that the B-mode image signal representing clutter is removed. For imaging applications associated with small vessels, a lower weight value may be used for high Doppler image signals for a more desirable or expected appearance.

The resulting weighted or modulated Doppler image signal then modulates the B-mode image signal. By multiplying the weight with the Doppler image signal and subtracting the result from 1, low Doppler values have little impact on the B-mode image signal, resulting in enhancement of the B-mode image signal. For high values of the Doppler image signal, the B-mode image signal is reduced or suppressed even for high value B-mode signals. For example where there is strong flow, the weight is selected as a high or close to unity value. As a result the B-mode image signal is multiplied or modulated by a substantially zero value, resulting in display indicia representing the absence of signal, such as black associated with a vessel. When there is weak flow, such as associated with flash, the tissue signal is maintained or slightly reduced relative to other tissue signals. Normal Doppler gain could also be used. However, normal Doppler gain may not be flow signal dependent but more uniformly increase/decrease sensitivity.

The modulated non-linear function described above substantially maintains or has little impact on the portion of the B-mode image signal associated with stationary tissue and substantially suppresses portions of the B-mode image signal associated with flow (i.e. enhancing the stationary tissue image signal relative to the B-mode image signal associated with flow). The thresholding, clutter filtering and/or other processes for removing Doppler image signals associated with tissues prevent undesired alteration of stationary tissue signals. The combination function above substantially suppresses the Doppler image signals associated with tissue given the low or substantially zero valued Doppler signals. As a result, where the B-mode image signals indicate tissue signals in a small vessel location, the combination substantially suppresses the B-mode image signals associated with the small vessel location. The resulting low value or value indicating an absence of signal more likely identifies the small vessel in the resulting B-mode image. In general, B-mode image signals associated with Doppler image signals having values within about an upper third of a range of possible Doppler image signals are suppressed. Other suppression ranges, such as an upper half, may be used based on the adaptive waiting. "About" is used to account for the gradual change in the normalized weighting function modulating the B-mode image signal. Using the combination function above, elevation artifacts in the B-mode image signal are substantially suppressed as a function of the Doppler image signal.

The output of the combination function discussed above is a display indicia representing tissue. The display indicia are used for gray-scale imaging or are generated as a gray-scale value. For example, the combination function above is used for radiology imaging of substantially stationary tissue. "Substantially" is used to account for some tissue movement due to the cyclical blood flow, breathing or other slow movement. By multiplying the B-mode image signal with the weighted Doppler image signal, clutter and artifacts are removed. A higher B-mode image signal is generated where the Doppler image signal is low. The resulting radiology image better identifies small vessels and removes clutter from large vessels.

Modular, non-linear combinations of both B-mode and Doppler image signals are applied for color flow or Doppler imaging in an alternative embodiment. The Doppler image signal is multiplied by or modulated by a weighted B-mode image signal as given by:

$$D_{out}=D_{in}(1-\alpha B), \qquad (2)$$

where $D_{out}$ is a Doppler display indicia for color display, $D_{in}$ is the Doppler image signal, $\alpha$ is a weight and B is a normalized B-mode image signal.

As shown in the equation above, the B-mode image signal is modulated by the weight, $\alpha$. In one embodiment, the weight is selected or calculated from the B-mode image signal. In alternative embodiments, the weight is responsive to different values or is constant. The B-mode image signal is normalized prior to multiplication by the weighting. Alternatively, the weighted B-mode signal is normalized prior to subtraction from the 1 value. This modulated, non-linear combination of Doppler and B-mode image signals for Doppler imaging may improve identification of the flow boundary and reduce flash artifact. Display indicia represent color for the Doppler output. For Doppler power imaging, the boundaries more generally fade rather than providing a jagged looking boundary associated with the binary on/off decision of conventional Doppler imaging.

In one further embodiment, a B-mode image is generated using the combination discussed above for equation (1), a Doppler image is generated using the combination discussed above for equation (2), and the Doppler image is superimposed on the B-mode image. While one iteration is possible, multiple iterations may be used to refine an individual or the superimposed B-mode and Doppler images. For example, a B-mode image is generated using modulated, non-linear combination function for equation (1). The resulting B-mode image is then used for combination with the Doppler image signal to generate a Doppler image signal output of equation (2). In further iterations, the Doppler signal output is then used as a Doppler input to generate yet another B-mode image output using the combinations discussed above for equation (1). The adaptive weighting function may change as a function of the iteration, or may be the same. Multiple iterations may provide further reduction of clutter and identification of small vessel structures.

In yet further alternative embodiments, the combination for generating just a B-mode image or just a Doppler image is repeated. For example, B-mode and Doppler image signals are combined to generate a B-mode output. The B-mode output is then used as a B-mode input for combining with the Doppler image signal to generate yet another B-mode output signal.

Other forms of the combination function are possible. For example, a B-flow or grayscale output signal representing both tissue and fluid flow is provided using the combination function:

$$B_{out}=B_{in}+\alpha D.$$

The weight, $\alpha$, is either constant or adaptive. In one embodiment, the weight is adaptive as a function of the Doppler image signal, D, or the B-mode image signal, $B_{in}$. The weight is within the range zero to 1. The Doppler signal D is not normalized, but may be normalized. The Doppler image signal is modulated or multiplied with the weight. The weighted Doppler image signal and a B-mode image signal are then added. In alternative embodiments, a same or different weight is applied to the B-mode image signal. A gray scale or B-mode output signal is provided for representing both flow and tissue. The adaptive combination provides good resolution, sensitivity and penetration by smoothly blending Doppler information with the B-mode information. This B-flow image may be used for various applications, such as imaging contrast agents. In alternative embodiments, the display indicia resulting from the summation combination function include color information. In one embodiment, $\alpha=0.5$. This constant value provides enough contrast to the flow signal over the surrounding tissue without removing desired information.

Various applications benefit from the combinations discussed above. Clutter is removed from large vessels, more small vessels are visible, tissue contrast is enhanced, flash artifact is reduced and the flow pattern appears smoother. In vascular imaging, the clutter inside the carotid artery, which is often artificially adjusted out by the user changing depth gain controls, is reduced and may be barely or not visible without manual adjustment. The intima and other physiology or pathology remains intact. Deep veins in the legs are more apparent in B-mode images since the vessels are less filled by clutter or other noise. More apparent deep veins are easier to locate. The valve inside the vein also becomes more visible, speeding up the exam process. Small vessels within the abdomen are more likely identified over the entire field of view. Kidney anatomy, such as pyramids, cortex, fatty tissue, small blood vessels and the urine collection system, are more readily observable for renal imaging. More information regarding the characteristics of a mass within the breast may be identified through better viewing of the blood supply system or small vasculature. In addition to the radiology applications described above, cardiac imaging may benefit by reduced elevation cluttering. Acoustic shadows from the lung are reduced. The apex and the chambers may be clear, especially at peak systole, and the coronary is more detectable. Better identification of small vessels reduces the impact and likelihood of false negative indicating a lack of vessel for B-mode images.

For contrast agent imaging, one or more of the combinations discussed above may improve the presentation or appearance of the image. By removing clutter and providing better identification of small vessels, 3D images may be better segmented and rendered with less noise. Quantification is assisted by higher resolution and cleaner boundary detection. Automatic boundary detection algorithms may be more robust by reduction in the flash artifact and B-mode artifacts.

While the invention has been described above by reference to various embodiments, it should be understood that many changes and modifications can be made without departing from the scope of the invention. For example, different combination functions and adaptive suppression or enhancing schemes may be used. Display indicia for different types of imaging may be adaptively suppressed or enhanced based on both the B-mode and Doppler image signals.

It is therefore intended that the foregoing detailed description be understood as an illustration of the presently preferred embodiment of the invention, and not as a definition of the invention. It is only the following claims, including all equivalents that are intended to define the scope of this invention.

What is claimed is:

1. A method for ultrasonically imaging with different signals for artifact reduction, adding missing small vessel information or enhancing tissue morphology the method comprising:
   (a) generating a Doppler image signal representative of an imaged region;
   (b) generating a B-mode image signal representative of the imaged region; and
   (c) generating individual display indicia representative of the imaged region as a modulated, non-linear function of both the Doppler and B-mode image signals, the non-linear function substantially maintaining portions of the B-mode image signal associated with stationary tissue and substantially suppressing portions of the B-mode image signal associated with flow.

2. The method of claim 1 wherein (c) comprises substantially suppressing the Doppler image signals associated with tissue.

3. The method of claim 2 wherein the B-mode image signals indicate tissue signals in a small vessel location and (c) comprises substantially suppressing the B-mode image signals associated with the small vessel location.

4. The method of claim 2 wherein (c) comprises substantially suppressing the B-mode image signals associated with Doppler image signals having values within about an upper third of a range of possible Doppler image signals.

5. The method of claim 1 wherein (c) comprises generating the individual display indicia as grey scale values.

6. The method of claim 1 wherein (c) comprises substantially suppressing elevation artifacts of the B-mode image signal as a function of the Doppler image signal.

7. The method of claim 1 wherein (c) comprises adapting the non-linear function in response to one of the Doppler and B-mode image signals.

8. The method of claim 7 wherein (c) comprises generating a higher B-mode image signal weight where the Doppler image signal is low.

9. The method of claim 1 wherein the imaged region comprises substantially stationary tissue.

10. A system for ultrasonically imaging with different signals for artifact reduction, the system comprising:
    a Doppler detector operable to generating a Doppler image signal representative of an imaged region;
    a B-mode detector operable to generating a B-mode image signal representative of the imaged region; and
    a processor operable to calculate individual display indicia representative of the imaged region as a modulated, non-linear function of both the Doppler and B-mode image signals.

11. The system of claim 10 wherein the processor is operable to calculate where the non-linear function substantially enhances portions of the B-mode image signal associated with stationary tissue and substantially suppressing portions of the B-mode image signal associated with flow.

12. The system of claim 10 wherein the processor is operable to modulate one of the Doppler and B-mode image signals as a function of the one of the Doppler and B-mode images signals.

13. The system of claim 12 wherein the processor is operable to multiply the modulated one of the Doppler and B-mode image signals by the other of the Doppler and B-mode image signals.

14. The system of claim 12 wherein the processor is operable to select a weight as a function of the Doppler image signal, weight the Doppler image signal with the weight, sum the weighted Doppler image signal with the B-mode image signal, and output a grey scale signal representing the sum of (e).

15. The system of claim 10 wherein the processor comprises a central processing unit.

16. A system for ultrasonically imaging with different signals for artifact reduction, the system comprising:
    a Doppler detector operable to generating a Doppler image signal representative of an imaged region;
    a B-mode detector operable to generating a B-mode image signal representative of the imaged region; and
    a mixing circuit connected with the B-mode and Doppler detectors, the mixing circuit operable to calculate individual display indicia representative of the imaged region as a modulated, non-linear function of both the Doppler and B-mode image signals.

17. The system of claim 16 wherein the mixing circuit comprises a plurality of separate devices in an application specific integrated circuit.

18. The system of claim 16 wherein the mixing circuit is operable to calculate where the non-linear function substantially maintains portions of the B-mode image signal associated with stationary tissue and substantially suppressing portions of the B-mode image signal associated with flow.

19. The system of claim 16 wherein the mixing circuit comprises a first multiplier operable to modulate one of the Doppler and B-mode image signals as a function of the one of the Doppler and B-mode images signals.

20. The system of claim 19 wherein the mixing circuit further comprises a second multiplier operable to multiply output of the first multiplier with the other of the Doppler and B-mode image signals.

21. The system of claim 19 wherein the first multiplier is operable to modulate the Doppler image signal as a function of the Doppler image signal, and the mixing circuit further comprising an adder operable to sum the output of the first multiplier with the B-mode image signal and output a grey scale signal.

22. A method for ultrasonically imaging with different signals for artifact reduction, the method comprising:
    (a) generating a Doppler image signal representative of an imaged region;
    (b) generating a B-mode image signal representative of the imaged region; and
    (c) generating individual display indicia representative of the imaged region as a modulated, non-linear function of both the Doppler and B-mode image signals, the non-linear function modulating one of the Doppler and B-mode image signals with a weighted other one of the B-mode and Doppler image signals.

23. The method of claim 22 wherein a weight of the weighted other one of the B-mode and Doppler image signals adapts as a function of a value.

24. The method of claim 23 further comprising:
   (d) adapting the weight as a function of the other one of the B-mode and Doppler image signals.

25. The method of claim 22 wherein (c) comprises substantially enhancing portion of the B-mode image signal associated with stationary tissue and substantially suppressing portions of the B-mode image signal associated with flow.

26. The method of claim 22 wherein (c) comprises multiplying the B-mode image signal with a weighted Doppler image signal.

27. The method of claim 22 wherein (c) comprises multiplying the Doppler image signal with a weighted B-mode image signal.

28. The method of claim 22 wherein (c) comprises:
   (c1) normalizing the other one of the B-mode and Doppler image signals within a range of zero to one;
   (c2) multiplying the normalized other one with a weight; and
   (c3) multiplying the normalized, weighted other one with the one of the Doppler and B-mode image signals.

29. The method of claim 22 wherein (c) comprises generating grey scale values.

30. A method for ultrasonically imaging with different signals for artifact reduction, the method comprising:

(a) generating a Doppler image signal representative of an imaged region;
   (b) generating a B-mode image signal representative of the imaged region; and
   (c) generating individual display indicia representative of the imaged region as a function of both the Doppler and B-mode image signals, one of the Doppler and B-mode image signals modulated by the one of the Doppler and B-mode images signals.

31. The method of claim 30 wherein (c) comprises modulating the Doppler image signal with a weight responsive to the Doppler image signal.

32. The method of claim 30 wherein (c) comprises modulating the B-mode image signal with a weight responsive to the B-mode image signal.

33. The method of claim 30 wherein (c) comprises multiplying the modulated one of the Doppler and B-mode image signals by the other of the Doppler and B-mode image signals.

34. The method of claim 30 wherein (c) comprises:
   (c1) selecting a weight as a function of the Doppler image signal;
   (c2) weighting the Doppler image signal with the weight;
   (c3) summing the weighted Doppler image signal with the B-mode image signal; and
   (c4) outputting a grey scale signal representing the sum of (e).

* * * * *